US00PP13382P2

(12) United States Plant Patent
Heims

(10) Patent No.: US PP13,382 P2
(45) Date of Patent: Dec. 17, 2002

(54) TIARELLA PLANT NAMED 'PINK SKYROCKET'

(75) Inventor: Daniel M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/990,638

(22) Filed: Nov. 20, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Klarquist Sparkman, LLP

(57) ABSTRACT

A new and distinct hybrid of Tiarella characterized a distinct leaf form and coloration and a distinct pink, cone-shaped inflorescence.

1 Drawing Sheet

The present invention relates to a new and distinct hybrid of Tiarella, of the family Saxifragaceae, which originated from a cross between unknown parents. This new Tiarella was one of many seedlings grown from select interspecific hybrids and species that were mass pollinated in the greenhouse in Canby, Oreg. From observation of the characteristics exhibited by the instant plant, it is most likely an interspecific hybrid. As such no species designations are given.

The new variety has been reproduced only by asexual propagation (division and micropropagation). Each of the progeny exhibits identical characteristics to the original plant.

This plant is characterized by the following:

1. Pink flowers on upright flower stalks of a distinct cone shape.
2. High flower number.
3. Compact habit.
4. Distinctive leaf form.

Asexual propagation by tissue culture using standard micropropagation techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

The FIGURE is a picture of Tiarella 'Pink Skyrocket' in bloom in the garden in Canby, Oreg.

DETAILED PLANT DESCRIPTION

The following is a detailed description of the new Tiarella hybrid based on observations of two-year-old plants grown in three-gallon pots in Canby, Oreg. The color descriptions are all based on The Royal Horticultural Society Colour Chart.

Botanical classification: Tiarella hybrid.
Cultivar name: 'Pink Skyrocket'.
Plant:
- *Type*.—Herbaceous perennial.
- *Hardiness*.—USDA Zones 5 to 9.

- *Form*.—Basal clump.
- *Size*.—40 cm wide and 18 cm high.

Foliage:
- *Type*.—Simple.
- *Arrangement*.—Rosette.
- *Shape*.—Ovate, palmatifid.
- *Lobing*.—Usually 5 and sometimes 7 parted to ¾ of the blade, the terminal lobe the longest, and lobes lacerate.
- *Margins*.—Palmatifid, lacerate.
- *Venation*.—Palmate.
- *Apex*.—Acuminate.
- *Base*.—Cordate.
- *Blade size*.—Variable, 5 to 8.5 cm long and 4.5 to 8 cm wide.
- *Texture*.—Rough.
- *Aspect*.—Matte.
- *Surface*.—Hirsute top and bottom.
- *Petiole length*.—10 to 17.2 cm.
- *Petiole texture*.—Strongly pubescent.
- *Petiole color*.—Greyed Orange 177A.
- *Leaf color*.—Spring new growth is Yellow Green 146B on the top surface and closest to Yellow Green 148A on the bottom. Summer color is Green 137A with Yellow Green 148A on the bottom. Winter color has Brown 200A mixed in the leaf. The pattern color is Greyed Purple 183A or 187A.

Inflorescence:
- *Type*.—Raceme.
- *Shape*.—Conical due to short spacing between pedicels.
- *Flower number*.—50 blooms per raceme and about 70 racemes blooming in the first flush.
- *Bloom period*.—April to May with sporadic rebloom throughout the summer and fall.
- *Peduncle*.—With 0 to one lobed cauline leaf. Height — 27 cm. Width — 2 mm. at the widest point. Color — Yellow green 146B in shade or Greyed Orange 177A in sun. Texture — Hispid.
- *Pedicel*.—Length — 0.6 cm. Texture — Puberulent. Color — Greyed Red 182B.

Flower bud:
- *Size*.—0.3 cm wide and 0.25 cm deep.
- *Description*.—Ovoid.
- *Color*.—Pink, Red 49C.

Flower:

*Type*.—Perfect, actinomorphic, sepals petaloid.

*Shape*.—Rotate, with stamens extruded.

*Petal and sepal number*.—5 petals, 5 fused sepals.

*Flower size*.—0.7 cm. wide and 0.5 cm. deep including stamens.

*Petal shape*.—Lanceolate with a clawed base.

*Petal size*.—0.3 cm long and 0.05 cm. wide.

*Petal color*.—New petals are pink, Red 49D, fading when mature to White 155D.

*Calyx*.—Petaloid, parted almost to the base.

*Calyx size*.—0.3 cm. wide and 0.1 cm. deep.

*Calyx color*.—Red 49D fading to White 155D.

*Stamens*.—10.

*Filaments*.—White 155A.

*Anthers undehisced*.—Orange Red 31C.

*Pollen color*.—Greyed Orange 167B.

*Pistil*.—White 155A.

*Fragrance*.—None.

Fruit:

*Type*.—A one-celled capsule, beak-like, composed of two unequal parts.

*Size*.—0.4 cm long.

*Color*.—Grey-Brown 199B.

Seeds:

*Color*.—Black 202A.

*Shape*.—Minute, linear.

*Fertility*.—Fertile.

Disease resistance: This new hybrid shows good mildew tolerance, the main problem for Tiarella.

Comparisons with Similar Tiarella

Compared with Tiarella 'Black Velvet' (U.S. Plant Pat. No. 12,348), Tiarella 'Pink Skyrocket' has pink flowers and buds, a more compact plant habit, and narrower leaf lobing.

I claim:

1. A new and distinct hybrid of Tiarella plant substantially as shown and described, characterized by a distinct leaf form and coloration and a distinct pink, cone-shaped inflorescence.

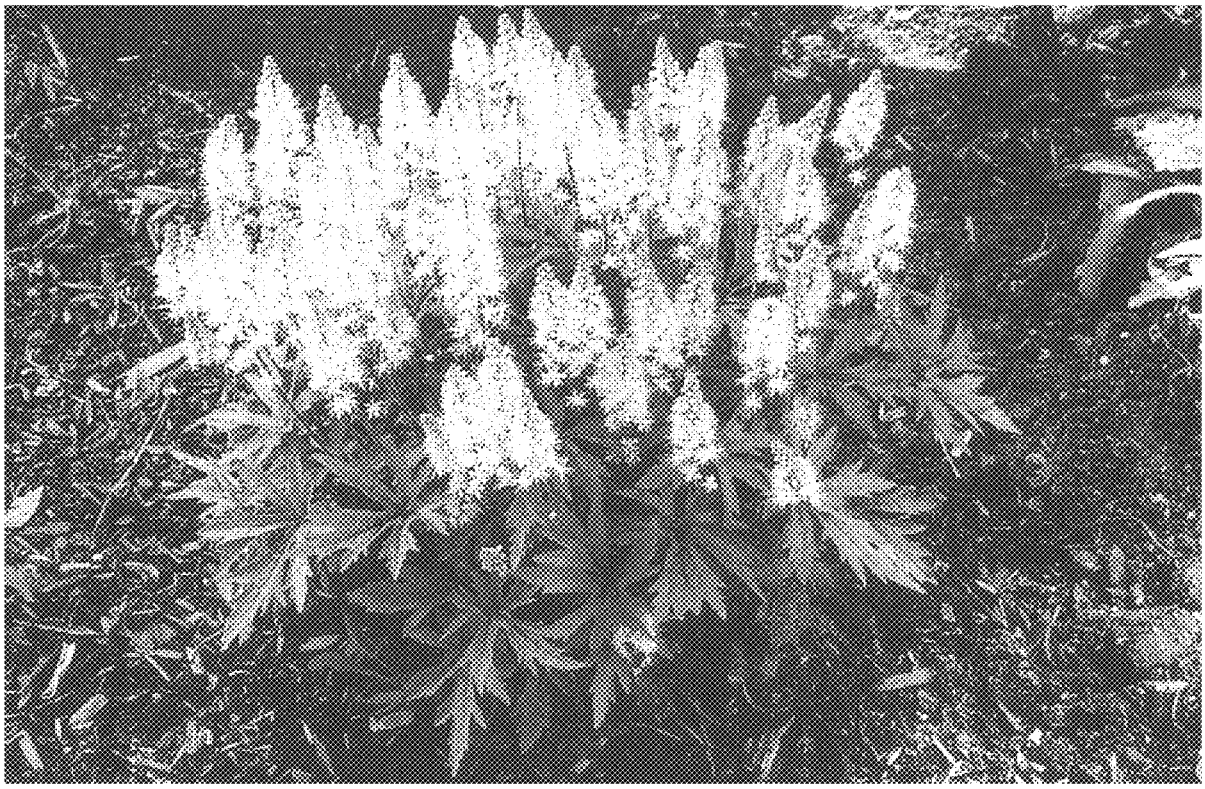

* * * * *